(12) United States Patent
Fix et al.

(10) Patent No.: US 8,418,527 B2
(45) Date of Patent: Apr. 16, 2013

(54) FIELD EFFECT TRANSISTOR GAS SENSOR HAVING A HOUSING AND POROUS CATALYTIC MATERIAL CONTAINED THEREIN

(75) Inventors: Richard Fix, Gerlingen (DE); Markus Widenmeyer, Schoenaich (DE); Alexander Martin, Ludwigsburg (DE); Dieter Elbe, Sachsenheim (DE)

(73) Assignee: Robert Bosch GmbH, Stuttgart (DE)

( * ) Notice: Subject to any disclaimer, the term of this patent is extended or adjusted under 35 U.S.C. 154(b) by 396 days.

(21) Appl. No.: 12/733,141

(22) PCT Filed: Jul. 30, 2008

(86) PCT No.: PCT/EP2008/060021
§ 371 (c)(1),
(2), (4) Date: Feb. 11, 2010

(87) PCT Pub. No.: WO2009/027168
PCT Pub. Date: Mar. 5, 2009

(65) Prior Publication Data
US 2010/0139365 A1   Jun. 10, 2010

(30) Foreign Application Priority Data
Aug. 29, 2007   (DE) .......................... 10 2007 040 726

(51) Int. Cl.
*G01N 7/12* (2006.01)
*G01N 27/414* (2006.01)

(52) U.S. Cl.
USPC ......................................... 73/31.06; 257/253

(58) Field of Classification Search .................. 73/31.06; 257/253
See application file for complete search history.

(56) References Cited

U.S. PATENT DOCUMENTS

| 4,931,851 A | 6/1990 | Sibbald et al. |
| 4,944,273 A * | 7/1990 | Baresel et al. ................. 123/703 |
| 6,044,689 A | 4/2000 | Yoshida et al. |
| 2006/0055392 A1* | 3/2006 | Passmore et al. ............ 324/71.1 |
| 2010/0132788 A1* | 6/2010 | Petrat et al. .................... 136/256 |

FOREIGN PATENT DOCUMENTS

| DE | 35 19 435 | 12/1986 |
| DE | 44 03 152 | 8/1995 |
| DE | 100 43 089 | 3/2002 |
| DE | 101 21 262 | 11/2002 |
| DE | 102 60 857 | 7/2004 |
| DE | 103 46 071 | 4/2005 |
| DE | 10 200 019638 | 11/2005 |
| DE | 10 2004 019 641 | 11/2005 |
| DE | 10 2005 008 051 | 8/2006 |
| DE | 102007018431 A1 * | 10/2008 |
| EP | 0 237 277 | 9/1987 |
| JP | 07 0551577 | 2/1995 |
| WO | WO 2008128821 A1 * | 10/2008 |

\* cited by examiner

*Primary Examiner* — Lisa Caputo
*Assistant Examiner* — Punam Roy
(74) *Attorney, Agent, or Firm* — Kenyon & Kenyon LLP

(57) ABSTRACT

A gas sensor for determining gas components in gas mixtures, e.g., for exhaust gases of internal combustion engines, includes a housing and a sensor element configured as a field effect transistor which has source, drain, and gate electrodes applied on a semiconductor substrate. A porous, catalytically active material is provided inside the housing of the gas sensor.

14 Claims, 2 Drawing Sheets

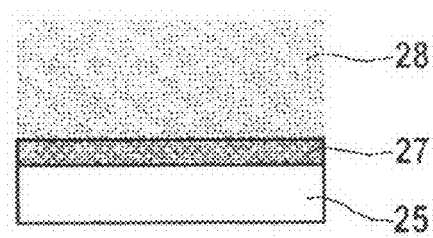
Fig. 1b
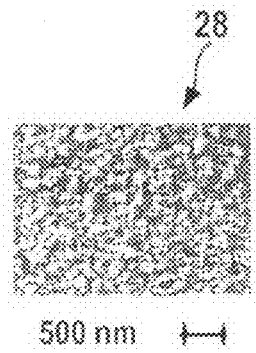
Fig. 2
Fig. 3
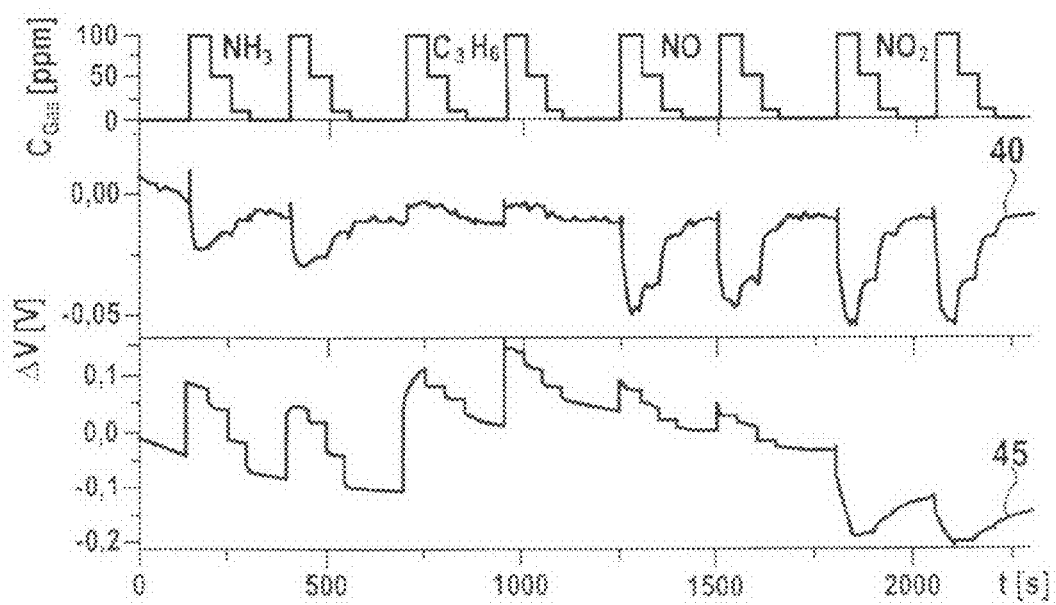

FIELD EFFECT TRANSISTOR GAS SENSOR HAVING A HOUSING AND POROUS CATALYTIC MATERIAL CONTAINED THEREIN

BACKGROUND OF THE INVENTION

1. Field of the Invention

The present invention relates to a gas sensor for determining gas components in gas mixtures, e.g., in the exhaust gas of internal combustion engines.

2. Description of Related Art

Field-effect transistors are used, among other things, in determining gas components in gas mixtures. For example, a gate electrode of the field-effect transistor reacts sensitively to gas components to be determined, thereby triggering a change in a control voltage applied to the gate electrode. The occurring change in the current flow resulting between the source electrode and the drain electrode is detected and associated with the concentration of a gas component.

If gas components are determined in exhaust gases of internal combustion engines, the determination of individual gas components is impaired by cross sensitivities to other gas components. In order to largely prevent this impairment of the measuring signals by interfering gas components, it is known from published German patent document DE 10 2004 019 641 A1, for example, to provide an FET-based gas sensor with a gas channel for diffusing a measuring gas to a gas-sensitive layer, an electrochemical element being introduced into the gas channel which is used for converting interfering gases.

BRIEF SUMMARY OF THE INVENTION

An object of the present invention is to provide a gas sensor which allows the independent determination of selected gas components of a gas mixture largely without cross sensitivities to other gas components.

In addition to a sensor element, which is designed as a field effect transistor, the gas sensor includes a porous, catalytically active layer. This porous, catalytically active layer is used for decomposing gas components contained in the gas mixture which would impair the determination of gas components to be detected. The great advantage of this system is, compared to specific embodiments of the related art, that the installation of an electrochemical element for eliminating undesirable gas components may be omitted and, at the same time, the sensitivity of the gas sensor to gas components to be detected is improved.

It is an advantage if the porous, catalytically active layer includes a ceramic material having a high BET surface. In this way, high catalytic activity of the porous, catalytically active layer can be achieved.

It is furthermore advantageous if the porous, catalytically active layer has a layer thickness of 2μ to 20 μm. On the one hand, due to the minimum layer thickness of 2 μm, a sufficient catalytic effect is achieved in this way; on the other hand, the layer thickness of the porous, catalytically active layer is limited in such a way that it does not put up an exceedingly high diffusion resistance against a diffusing gas mixture.

According to a further advantageous example embodiment, the porous, catalytically active layer is designed as an oxidation catalyst. This allows in an advantageous manner the oxidation of hydrocarbons, hydrogen or nitrogen monoxide and nitrous oxide into carbon dioxide, water, and nitrogen dioxide, respectively. In this way, only nitrogen dioxide is present as the gas component to be detected in a gas mixture reaching the sensitive area of the gas sensor; water and carbon dioxide, which are also formed, do not affect its determination.

In addition, it is advantageous if the porous, catalytically active layer in the form of a diffusion barrier is situated flat on a gate electrode of the sensor element designed as a field effect transistor. In this way, it is effectively ensured that only a gas mixture, which is pretreated with the aid of the porous, catalytically active layer, may advance to the surface area of the gate electrode of the field effect transistor.

According to a particularly advantageous example embodiment of the present invention, the gate electrode of the field effect transistor is provided with a gas-sensitive coating, on which the porous, catalytically active layer may be positioned as a diffusion barrier. It has been found that gate electrodes, which have a gas-sensitive coating, have a definitely higher selectivity and sensitivity with regard to the signal quality of corresponding measuring signals.

BRIEF SUMMARY OF THE SEVERAL VIEWS OF THE DRAWING

FIG. 1b shows a schematic sectional illustration of a transistor gate of a gas sensor according to an alternative to the first example embodiment of the present invention.

FIG. 2 shows a photographic illustration of the top view onto a transistor gate which has a platinum coating.

FIG. 3 shows plotting of the measuring signal of two gas sensors against time and the concentration of gas components to be determined, one of the gas sensors having a catalytic coating as an integral part of the transistor gate.

DETAILED DESCRIPTION OF THE INVENTION

Figure 1A:
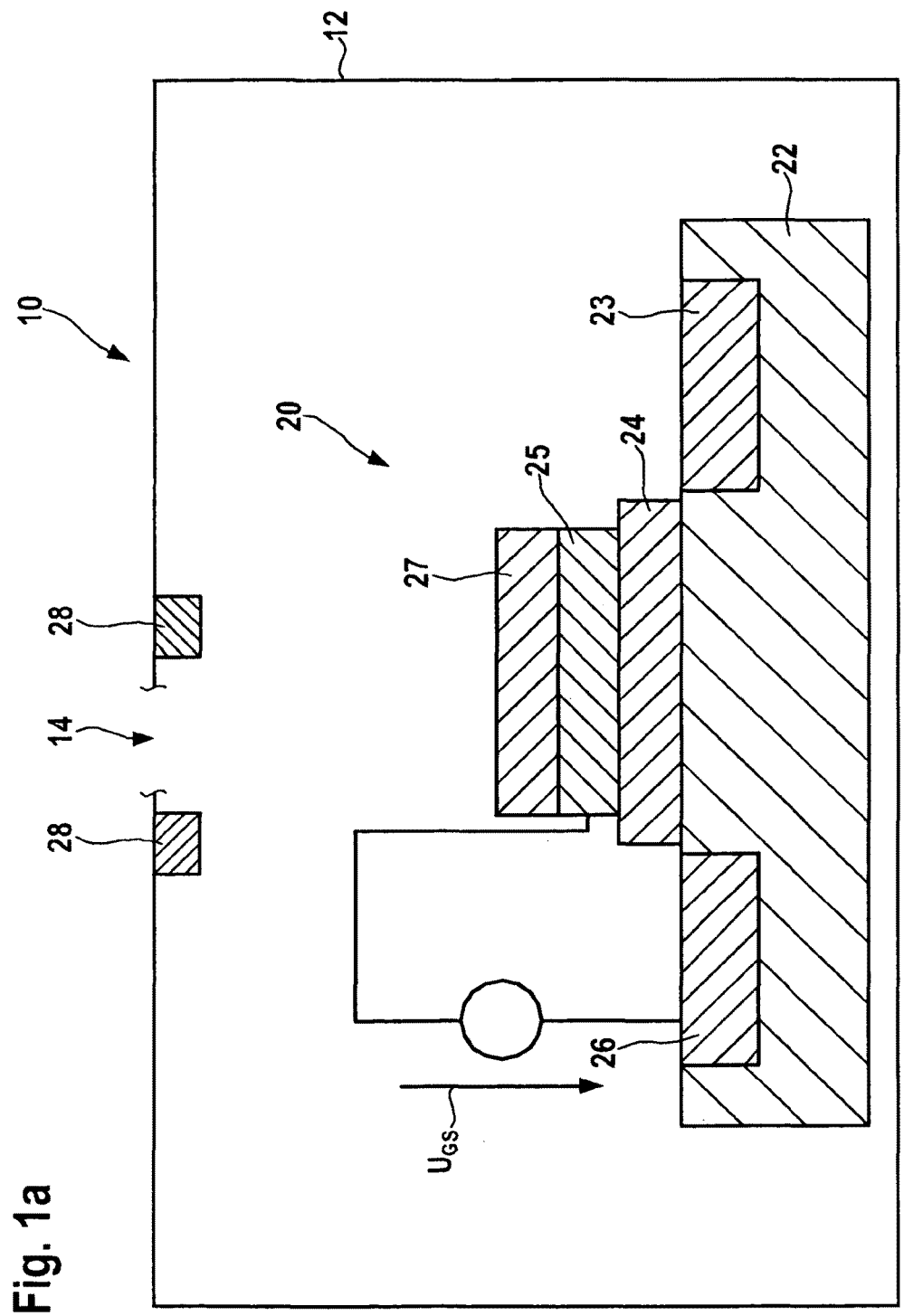
FIG. 1a shows a schematic sectional illustration of a gas sensor according to a first example embodiment of the present invention.

FIG. 1a schematically shows a gas sensor according to a first example embodiment of the present invention. In a housing 12, gas sensor 10 includes a sensor element 20 which is designed in the form of a field effect transistor (FET) or as a chemically sensitive field effect transistor (chem-FET), for example. Field effect transistor 20 includes a semiconductor substrate 22 which is made of gallium nitride, aluminum nitride, gallium aluminum nitride, or silicon carbide. Semiconductor substrate 22 is provided with a so-called source electrode 26 and a so-called drain electrode 23. Furthermore, sensor element 20 includes a gate electrode 25 which is in physical contact with semiconductor material 22 via an insulating layer 24. Insulating layer 24 is used here for preventing gate leakage currents and thus possible electromigration. In this way, the electrical operation is ensured and simple signal analysis is made possible.

If gate electrode 25 is designed to be suitably sensitive for gas components to be measured, then a voltage $U_{GS}$, applied between source electrode 26 and gate electrode 25, changes as a function of the concentration of the gas component to be determined. For this purpose, gate electrode 25 is provided with a preferably porous coating 27 of a noble metal or a noble metal-metal oxide mixed material, as shown in FIG. 1b. The metallic material of porous coating 27 is preferably selected from the heavy or high atomic number transition elements such as niobium, tantalum, molybdenum, tungsten, rhenium, ruthenium, osmium, rhodium, iridium, palladium, platinum, silver, or gold or mixtures of same. Moreover, electrically conductive compounds such as nitrides, carbides, or silicides of the transition elements such as tungsten silicide or tantalum silicide are suitable, for example. Cermets are particularly suitable as a noble metal-metal oxide mixed material which, in addition to the above-mentioned transition elements or their carbides or silicides, contain a ceramic component such as aluminum oxide, silicon oxide, zirconium dioxide, molybdenum oxide, tungsten oxide, germanium dioxide, titanium dioxide, boron oxide or oxides of the alkaline earth metals or rare earth metals, such as in particular magnesium oxide, lanthanum oxide, or cerium oxide. FIG. 2 shows a photographic top view onto gate electrode 25 having a porous platinum coating.

The resulting gate electrode has an electrical conductivity in the range of <100 kOhm, for example, in particular oxidation-stable noble metals such as platinum, gold, iridium, rhenium, and mixtures of same being used as the electrode material of gate electrode 25. Moreover, electrically conductive compounds such as nitrides, carbides, or silicides of the transition elements such as tungsten silicide or tantalum silicide, for example, are suitable. However, porous coating 27 and gate electrode 25 are made from different materials.

As an alternative, gate electrode 25 itself is made of the material of coating 27 so that application of a separate coating 27 may be omitted.

For example, if gas sensor 10 is used for determining gas components of a combustion exhaust gas, it is exposed to a plurality of different gas species which triggers a complex sensor signal so that selective detection of individual gas components may prove to be problematic.

To counteract this problem, gas sensor 10 includes, inside its housing 12, a catalytically active material 28 which is used in particular for eliminating individual gas components of a gas mixture toward which sensor element 20 shows an undesirable cross-sensitivity. These undesirable gas components are catalytically converted on catalytically active material 28 into gas components which do not interfere with a measurement of the gas components to be determined.

If catalytically active material 28 is designed as an oxidation catalyst, for example, reductively acting gaseous components of the gas mixture are converted into their highest possible oxidation state. For example, hydrocarbons are oxidized into carbon dioxide and water. Moreover, carbon monoxide is converted into carbon dioxide. However, the response of gas sensor 10 to water and carbon dioxide is almost non-sensitive.

Furthermore, nitrogen oxides such as nitrogen monoxide and nitrogen dioxide contained in the gas mixture are detected at gate electrode 25 in the form of a nitrogen oxide measuring signal.

This catalytical oxidation process proceeds predominantly during a sensor operation in the temperature range between 400° C. and 650° C., preferably between 480° C. and 550° C.

For example, catalytically active material 28, as shown in FIG. 1b, may be provided as the coating on gate electrode 25 and may cover it at least partially, but may preferably cover it essentially completely. In this way, catalytically active material 28 acts as a diffusion barrier preventing a gas mixture to be measured to reach the surface area of gate electrode 25.

It is alternatively possible to position catalytically active material 28 in the form of a coating on or in a gas inlet aperture 14 of housing 12 of gas sensor 10.

An additional alternative is to position catalytically active material 28 on an interior wall of the housing or inside a feed line for a gas mixture to be measured between gas inlet aperture 14 and gate electrode 25. For example, FIG. 1a shows a specific embodiment in which catalytically active material 28 is positioned annularly around gas inlet aperture 14. Catalytically active material 28 is thus positioned in particular in such a way that, prior to the actual measuring process on the surface area of gate electrode 25, a gas mixture to be measured has already passed catalytic material 28 or had at least contact with it and has thus been chemically converted, at least partially.

A third alternative is to integrate catalytic material 28 into a coating which is positioned in a suitable position on semiconductor substrate 22 or on a substrate enveloping the same.

Catalytically active material 28 is preferably composed of a large-surface oxide such as cerium oxide, zirconium dioxide, aluminum oxide, silicon dioxide, a zeolite or mixtures of same. This ceramic substrate has a BET surface area of 150 $m^2/g$ to 250 $m^2/g$, for example. As the catalytically active component, catalytically active material 28 contains in particular noble metals such as platinum, rhodium, palladium, iridium or mixtures of same. Furthermore, catalytical promoters such as alkaline metals, alkaline earth metals, or rare earth metals are provided, for example. Catalytically active material 28 forms a catalytic coating separate from gate electrode 25 which differs from that of gate electrode 25 with regard to its material.

In a further example embodiment, catalytically active material 28 is designed as a so-called $NH_3$-SCR catalyst (Selective Catalytic Reduction Catalyst). As catalytically active components it contains tungsten, molybdenum, titanium, or vanadium oxides, for example. It may also contain transition metal-containing zeolites. The particular advantage of this type of catalyst is that ammonia and nitrogen oxides are converted at a 1:1 ratio so that a difference signal between the original nitrogen oxide and ammonia content results as the measuring signal.

A further advantage is to provide copper, silver, gold, or iridium, or mixtures of same and also oxides of manganese, tantalum, or nimobium as the catalytically active component of catalytically active material 28. The advantage of this specific embodiment is that hydrocarbons as components of the gas mixture may be selectively oxidized and thus eliminated. Moreover, it is a subject matter of the present invention to combine materials of the above-mentioned three alternative specific embodiments of the catalytically active material.

In an advantageous example embodiment of the present invention, for example, a gate electrode 25 made of or coated by a platinum-containing cermet, which contains, for example, aluminum oxide or cerium oxide as a ceramic component, is coated using a suspension of fine-grained aluminum oxide having a BET surface area of, for example, 250 $m^2/g$ which contains 10 percent by weight platinum. The aluminum oxide particles have a diameter of approximately 1 µm, for example. The layer formed is, for example, 5 µm to 15 µm thick, in particular 8 µm to 10 µm thick. Catalytically active material 28 may alternatively be applied in the form of a thick film by dispensing a washcoat suspension, by spinning on a lacquer coat containing a washcoat and subsequent structuring, for example, in a lift-off process or by imprinting with the aid of a screen-printing method. The above-mentioned method alternatives are followed by a heat treatment in the temperature range of 250° C. to 650° C., preferably in the temperature range of 450° C. to 600° C. Due to the retention time in an appropriate furnace of between 15 minutes and 24 hours, this results in an activation of the catalytically active components as well as in sintering of the ceramic particles on whose surface area the catalytically active components are located.

In a further exemplary embodiment, a gate electrode 25 made of platinum is provided with an oxidation catalyst in the form of platinum and/or rhodium supported on aluminum oxide. A comparison of the sensitivity of a gas sensor having a plain nano-platinum gate electrode and a gas sensor whose nano-platinum gate electrode has been provided with a coating in the form of an oxidation catalyst is illustrated in FIG. 3. Measuring curve 40 indicates here the measuring signal of a gas sensor whose gate electrode has a catalytically active material in the form of an oxidation catalyst and measuring curve 45 indicates the measuring signal of a gas sensor without a catalytically active coating. It is clearly apparent that measuring curve 40 shows a definitely smaller dependency on undesirable gas components in terms of measuring techniques such as propane, for example, and at the same time shows a selective sensitivity to nitrogen compounds such as ammonia, nitrogen monoxide and nitrogen dioxide and in particular to nitrogen oxides.

The gas sensor according to the present invention is suitable in particular for controlling exhaust gas after-treatment devices such as exhaust gas catalytic converters, diesel particle filters, and SCR systems.

What is claimed is:

1. A gas sensor for determining gas components in a gas mixture, the gas sensor comprising:
   a housing;
   a gas-sensitive element that includes at least one field-effect transistor; and
   a porous, catalytically active material provided inside the housing;
   wherein:
      the field-effect transistor includes source, drain, and gate electrodes applied to a semiconductor substrate; and
      the porous, catalytically active material contains a ceramic material having a BET surface area of 20 $m^2/g$ to 400 $m^2/g$.

2. A gas sensor for determining gas components in a gas mixture, the gas sensor comprising:
   a housing;
   a gas-sensitive element that includes at least one field-effect transistor; and
   a porous, catalytically active material provided inside the housing;
   wherein:
      the field-effect transistor includes source, drain, and gate electrodes applied to a semiconductor substrate; and
      a layer thickness of the porous, catalytically active material is 2 μm to 20 μm.

3. The gas sensor as recited in claim 1, wherein the porous, catalytically active material contains a noble metal as a catalytically active component.

4. The gas sensor as recited in claim 1, wherein the porous, catalytically active material contains one of an alkaline metal, an alkaline earth metal, or a rare earth metal as a promoter.

5. The gas sensor as recited in claim 1, wherein the porous, catalytically active material is an oxidation catalyst.

6. The gas sensor as recited in claim 1, further comprising:
   a heating element.

7. A gas sensor for determining gas components in a gas mixture, comprising:
   a housing;
   a gas-sensitive element that includes at least one field-effect transistor;
   a porous, catalytically active material provided inside the housing; and
   a feed line for supplying the gas mixture to the gas-sensitive element;
   wherein:
      the field-effect transistor includes source, drain, and gate electrodes applied to a semiconductor substrate; and
      the porous, catalytically active material is positioned inside the feed line as a diffusion barrier.

8. The gas sensor as recited in claim 7, wherein the diffusion barrier is situated flat on the gate electrode and at least partially covers the gate electrode.

9. The gas sensor as recited in claim 8, wherein the gate electrode includes one of a porous metal or a cermet layer.

10. The gas sensor as recited in claim 7, wherein a first field-effect transistor and a second field-effect transistor are provided, the first field-effect transistor including a first porous, catalytically active material and the second field-effect transistor including a second porous, catalytically active material different from the first porous, catalytically active material in material composition.

11. A gas sensor for determining gas components in a gas mixture, comprising:
    a housing;
    a gas-sensitive element that includes at least one field-effect transistor; and
    a porous, catalytically active material provided inside the housing;
    wherein:
       the field-effect transistor includes:
          source, drain, and gate electrodes applied to a semiconductor substrate;
          a gas-sensitive coating that is provided on the gate electrode, is made of a material different than a material of which the gate electrode is made, and is in direct physical contact with the electrode material of the gate electrode.

12. The gas sensor as recited in claim 11, wherein at least one of the gate electrode and the gas-sensitive coating contains at least one of rhenium, ruthenium, osmium, palladium, platinum, rhodium, iridium, silver and gold.

13. The gas sensor as recited in claim 11, wherein at least one of the gate electrode and the gas-sensitive coating includes pores having a diameter of 2 nm to 500 nm.

14. The gas sensor as recited in claim 11, wherein a first field-effect transistor and a second field-effect transistor are provided, the first field-effect transistor including a first porous, catalytically active material and the second field-effect transistor including a second porous, catalytically active material different from the first porous, catalytically active material in material composition.

* * * * *

UNITED STATES PATENT AND TRADEMARK OFFICE
CERTIFICATE OF CORRECTION

PATENT NO. : 8,418,527 B2  
APPLICATION NO. : 12/733141  
DATED : April 16, 2013  
INVENTOR(S) : Fix et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 396 days.

Signed and Sealed this
First Day of September, 2015

Michelle K. Lee
*Director of the United States Patent and Trademark Office*